US00PP28529P3

(12) United States Plant Patent
McGranahan et al.

(10) Patent No.: US PP28,529 P3
(45) Date of Patent: Oct. 17, 2017

(54) WALNUT TREE NAMED 'DURHAM'

(50) Latin Name: *Juglans regia*
Varietal Denomination: Durham

(71) Applicant: The Regents of the University of California, Oakland, CA (US)

(72) Inventors: Gale McGranahan, Davis, CA (US); Charles Leslie, Davis, CA (US)

(73) Assignee: The Regents Of The University Of California, Oakland, CA (US)

( * ) Notice: Subject to any disclaimer, the term of this patent is extended or adjusted under 35 U.S.C. 154(b) by 101 days.

(21) Appl. No.: 14/998,636

(22) Filed: Jan. 27, 2016

(65) Prior Publication Data

US 2017/0215313 P1 Jul. 27, 2017

(51) Int. Cl.
*A01H 5/08* (2006.01)

(52) U.S. Cl.
USPC ..... Plt./154

(58) Field of Classification Search
USPC ..... Plt./154
See application file for complete search history.

(56) References Cited

PUBLICATIONS

The Mar. 15, 2001 Test Agreement for Trees (No. 2001-5035) between Joe Contant and The Regents of The University of California, 5 pages.
The Sep. 1, 2002 Test Agreement for Trees (No. 2003-5005) between Driver Nursery, Inc. and The Regents of The University of California, 5 pages.
The Mar. 11, 2003 Test Agreement for Trees (No. 2003-5048) between Sierra Gold Nursery and The Regents of The University of California, 7 pages.
The Mar. 10, 2005 Test Agreement for Trees (No. 2005-5024) between Carriere & Sons and The Regents of The University of California, 7 pages.
The Apr. 26, 2005 Test Agreement for Trees (No. 2005-5021) between Golden Valley Nursery and The Regents of The University of California, 8 pages.
The Sep. 21, 2005 Test Agreement for Trees/Rootstocks (No. 2006-5005) between Whitney Warren Ranch/Joe Contant and The Regents of The University of California, 8 pages.
The Mar. 1, 2007 Test Agreement for Trees/Rootstocks (No. 2007-5021) between Deardorff Farm Management, Inc. and The Regents of The University of California, 7 pages.
The Aug. 1, 2009 Test Agreement for Trees (No. 2009-7007) between SCA Unicoque and The Regents of The University of California, 7 pages.
The Feb. 1, 2010 Test Agreement for Trees/Rootstocks (No. 2010-5002) between Carriere & sons and The Regents of The University of California, 7 pages.
The Feb. 1, 2010 Test Agreement for Trees/Rootstocks (No. 2010-5003) between David Scheuring and The Regents of The University of California, 7 pages.
The Mar. 1, 2010 Test Agreement for Trees/Rootstocks (No. 2010-5015) between Golden Valley Farms, Inc. and The Regents of The University of California, 7 pages.
The Aug. 1, 2010 Test Agreement for Trees/Rootstocks (No. 2010-5024) between The Burchell Nursery, Inc. and The Regents of The University of California, 7 pages.
The Feb. 1, 2011 Test Agreement for Trees (No. 2011-5006) between Sierra Gold Nurseries, Inc. and The Regents of The University of California, 7 pages.
The Apr. 1, 2011 Test Agreement for Trees/Rootstocks (No. 2011-5022) between FDS Farms and The Regents of The University of California, 7 pages.
The Feb. 1, 2012 Test Agreement for Trees/Rootstocks (No. 2012-5008) between Bert Crane Orchards, L.P. and The Regents of The University of California, 7 pages.
The Apr. 1, 2012 Test Agreement for Trees (No. 2012-5013) between David Scheuring and The Regents of The University of California, 7 pages.
The Feb. 1, 2013 Test Agreement for Trees (No. 2013-5011) between Cam Land Company, LP and The Regents of The University of California, 7 pages.
The Mar. 1, 2013 Test Agreement for Trees (No. 2013-5003) between Carriere Family farms, Inc. and The Regents of The University of California, 7 pages.
The Mar. 19, 2013 Test Agreement for Trees (No. 2013-5005) between Martinez Orchards, Inc. and The Regents of The University of California, 7 pages.
The Mar. 19, 2013 Test Agreement for Trees (No. 2013-5008) between Orestimba Nursery LLC and The Regents of The University of California, 7 pages.
The Mar. 19, 2013 Test Agreement for Trees (No. 2013-5013) between Dave Wilson Nursery, Inc. and The Regents of The University of California, 7 pages.
The Mar. 19, 2013 Test Agreement for Trees (No. 2013-5012) between Stuke Nursery Co., Inc. and The Regents of The University of California, 7 pages.
The Mar. 19, 2013 Test Agreement for Trees (No. 2013-5017) between Jerry K. Moore, Inc. dba Venice Hill Walnut Nursery and The Regents of The University of California, 5 pages.
The Feb. 1, 2014 Test Agreement for Trees (No. 2014-5003) between Steve Moffitt and The Regents of The University of California, 7 pages.
The Mar. 1, 2014 Test Agreement for Trees (No. 2014-5005) between R. Donald Norene and The Regents of The University of California, 7 pages.
The Mar. 1, 2014 Test Agreement for Trees (No. 2014-7005) between Il Noceto Soc. Coop. Agr. and The Regents of The University of California, 7 pages.
The Apr. 1, 2014 Test Agreement for Trees (No. 2014-7006) between Consorcio Viveros de Chile S.A. and The Regents of The University of California, 7 pages.
The Nov. 1, 2014 Test Agreement for Trees (No. 2014-7009) between Azienda Agricola Valier S.s. Soc. Agr. and The Regents of The University of California, 7 pages.

*Primary Examiner* — Anne Grunberg
(74) *Attorney, Agent, or Firm* — Morrison & Foerster LLP

(57) ABSTRACT

A new walnut variety (*Juglans regia*) designated as 'Durham' is provided. This variety has a harvest date 10 days earlier than walnut variety 'Chandler', and produces a walnut that is jumbo in size with light colored kernels.

11 Drawing Sheets

WALNUT TREE NAMED 'DURHAM'

Latin name: Botanical/commercial classification: *Juglans regia* new English walnut cultivar.

Varietal denomination: The varietal denomination of the claimed walnut variety is 'Durham'.

BACKGROUND OF THE INVENTION

In the walnut industry, it has long been recognized as desirable to provide walnut trees bearing large crops that are ripe for commercial harvesting and shipment early in the harvest season. In particular, the California walnut industry is in need of earlier harvesting walnut varieties, as the most commonly planted variety 'Chandler' (U.S. Plant Pat. No. 4,388) harvests late in the season (early to mid-October), which delays processing. 'Ivanhoe' (U.S. Plant Pat. No. 21,718) and 'Solano' (U.S. Plant Pat. No. 25,466) were recently released as early harvesting varieties, but both leaf relatively early and thus have greater exposure to wet spring conditions that are more conducive to bacterial blight. Further, the walnut industry desires walnut cultivars with light kernel color for marketing value. Thus, there exists a need for improved walnut varieties with mid-season harvest dates and desirable walnut characteristics.

SUMMARY OF THE INVENTION

The present invention relates to a new and distinct cultivar of walnut tree (*Juglans regia*) that has been denominated as 'Durham', and more particularly to a walnut variety that has a harvest date 10 days earlier than walnut variety 'Chandler' and that further produces a walnut that is jumbo in size and with light colored kernels.

It was found that the new *Juglans regia* cultivar 'Durham' exhibits the following combination of characteristics:

a) forms jumbo-sized walnuts that possess light-colored kernels;
b) bears nuts with shells that are smooth, oval, light colored, well-sealed, and attractive in appearance;
c) bears fruit both terminally and laterally;
d) yields a crop that can be harvested approximately 10 days before 'Chandler'; and
e) is protandrous, bearing male flowers before female flowers.

Walnut variety 'Durham' was originally identified as a progeny of a controlled pollination between 'Chandler' and 'PI159568' (unpatented), this controlled pollination taking place during Year 1 in Davis, Calif. Seeds resulting from this cross were planted in a nursery in Year 2 and were established in a seedling trial in Year 3. In this seedling trial, 21 trees resulting from the cross above, along with other trees in the walnut breeding program, were carefully observed and evaluations began in Year 6. When these trees began to bear nuts, data was collected annually on leafing date; first, peak, and last female flower bloom; first, peak, and last male bloom; blight severity; and yield (FIG. 11 and TABLE 2). Nuts were sampled, cracked, and data was collected on shell appearance, shell thickness, shell integrity, shell strength, nut weight, kernel weight, percent kernel, ease of kernel removal, kernel color, and percent kernel shrivel (FIG. 11 and TABLE 2). A single tree, designated as selection 'UC93-028-20', was selected in Year 9 from among progeny of the controlled cross above based on its superior attributes, which included its mid-season harvest date, good yields, plump light-colored kernels, and attractive shell appearance.

Selection 'UC93-028-20' was selected as a candidate for release as the variety 'Durham'.

Walnut variety 'Durham' has been asexually propagated by grafting on 'Paradox' rootstock at several locations including 1) in selection blocks at Davis, Chico, and Parlier, Calif., 2) in grower field trials at Durham, Wheatland, Yuba City, Artois, East Biggs, Woodland, Modesto, and Merced, Calif., and 3) at major California walnut nurseries. The distinctive characteristics of 'Durham' have been found to be stable and are transmitted to the new trees when asexually propagated.

BRIEF DESCRIPTION OF THE TABLES

TABLE 1 shows 'Durham' trial locations, number of trees at each site, and number of years of data collected at each location.

TABLE 2 shows a key to evaluation traits presented in FIG. 11.

BRIEF DESCRIPTION OF THE DRAWINGS

FIG. 11 illustrates the summarized phenology, tree, and nut evaluations for walnut variety 'Durham', both parents of 'Durham' ('Chandler' and 'PI159568'), and several comparison cultivars. Bolded traits illustrate especially desirable traits of 'Durham'.

DETAILED BOTANICAL DESCRIPTION

The following is a detailed botanical description of walnut variety 'Durham'. The description is based on both 1) an ungrafted 'Durham' walnut tree on its own roots, and 2) trees subsequently grafted on 'Paradox' rootstock growing in selection blocks in Davis, Chico, and Parlier, Calif., as well as in grower trials near Woodland, Durham, Wheatland, and Yuba City, Calif. The first data was collected on the own-rooted tree from Year 6 (age 4 years) to Year 13 (age 11 years). Data from Years 12 to 23 were collected from grafted trees. A summary of the trials where 'Durham' has been evaluated are presented in TABLE 1. The Munsell Color Charts for Plant Tissues is used in the identification of color. Also, common color terms are to be accorded their ordinary dictionary significance.

Botanical classification: *Juglans regia.*

Female parent: 'Chandler'.

Figure 1:
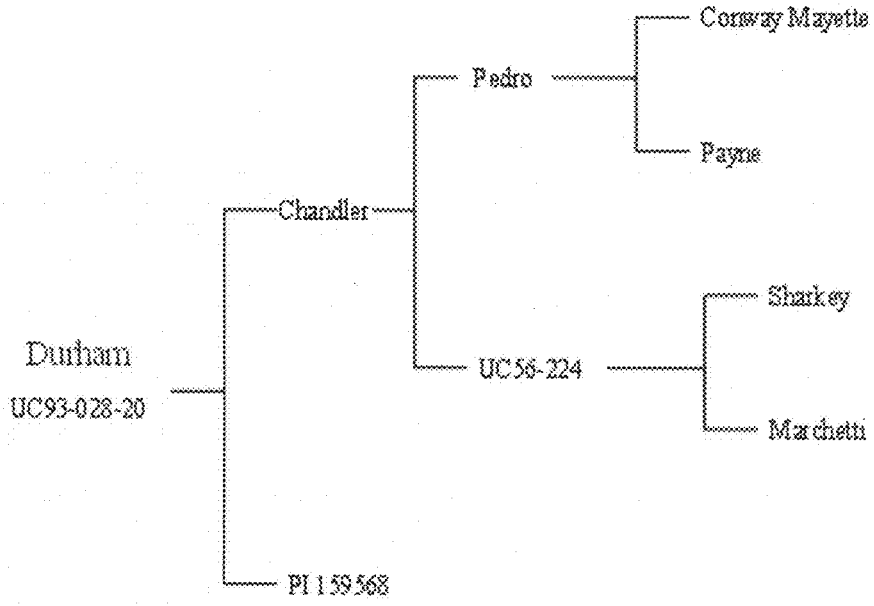
FIG. 1 illustrates the breeding pedigree of the walnut variety 'Durham'.

Male parent: 'PI159568'. The breeding pedigree of walnut variety 'Durham' is presented in FIG. 1. Compared to 'Durham', the parent 'PI159568' has an earlier harvesting date, but bears nuts only at the terminal positions on new branches. The parent 'Chandler' is later harvesting than 'Durham' and nuts have a lower percent kernel fill (FIG. 11 and TABLE 2).

Figure 2:
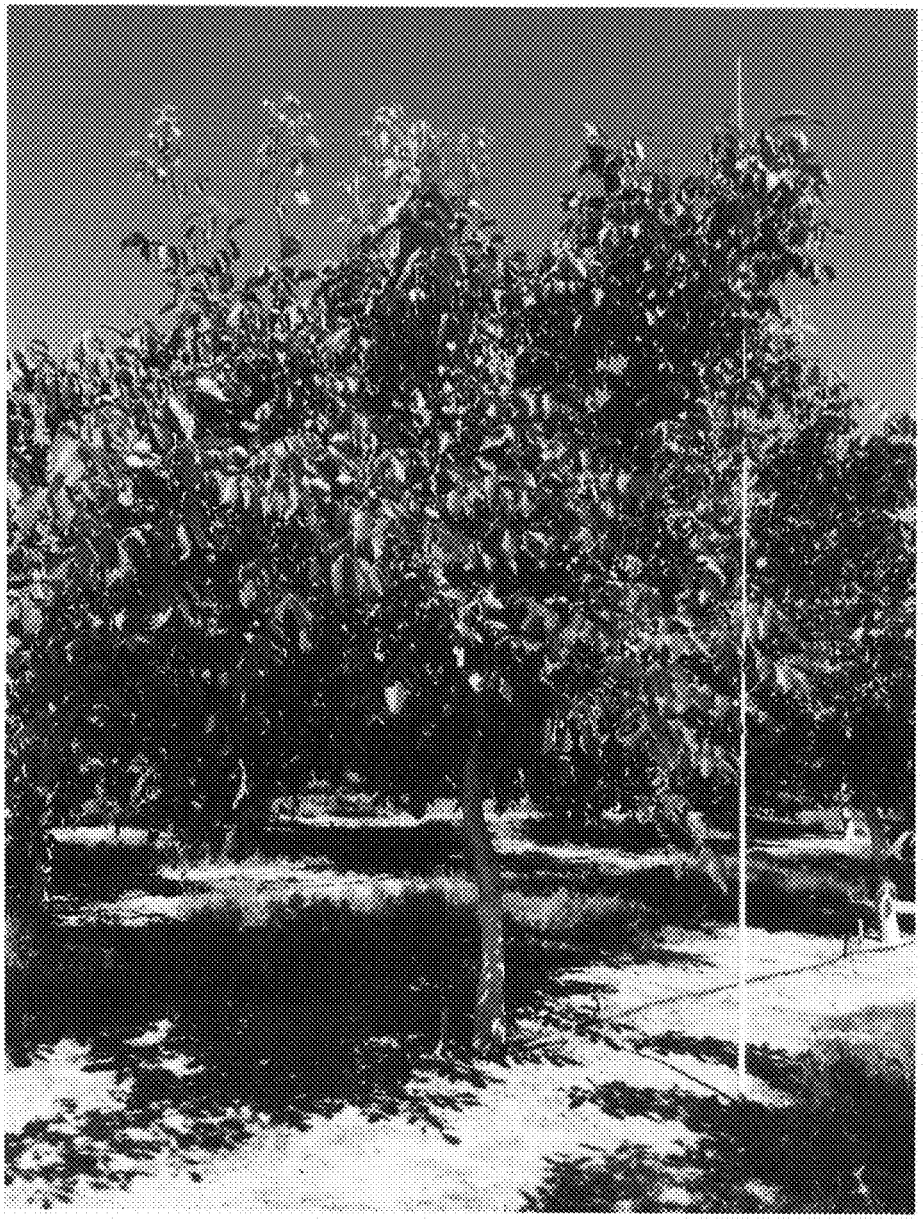
FIG. 2 illustrates a tree of walnut variety 'Durham' at 6 years old.
Figure 3:
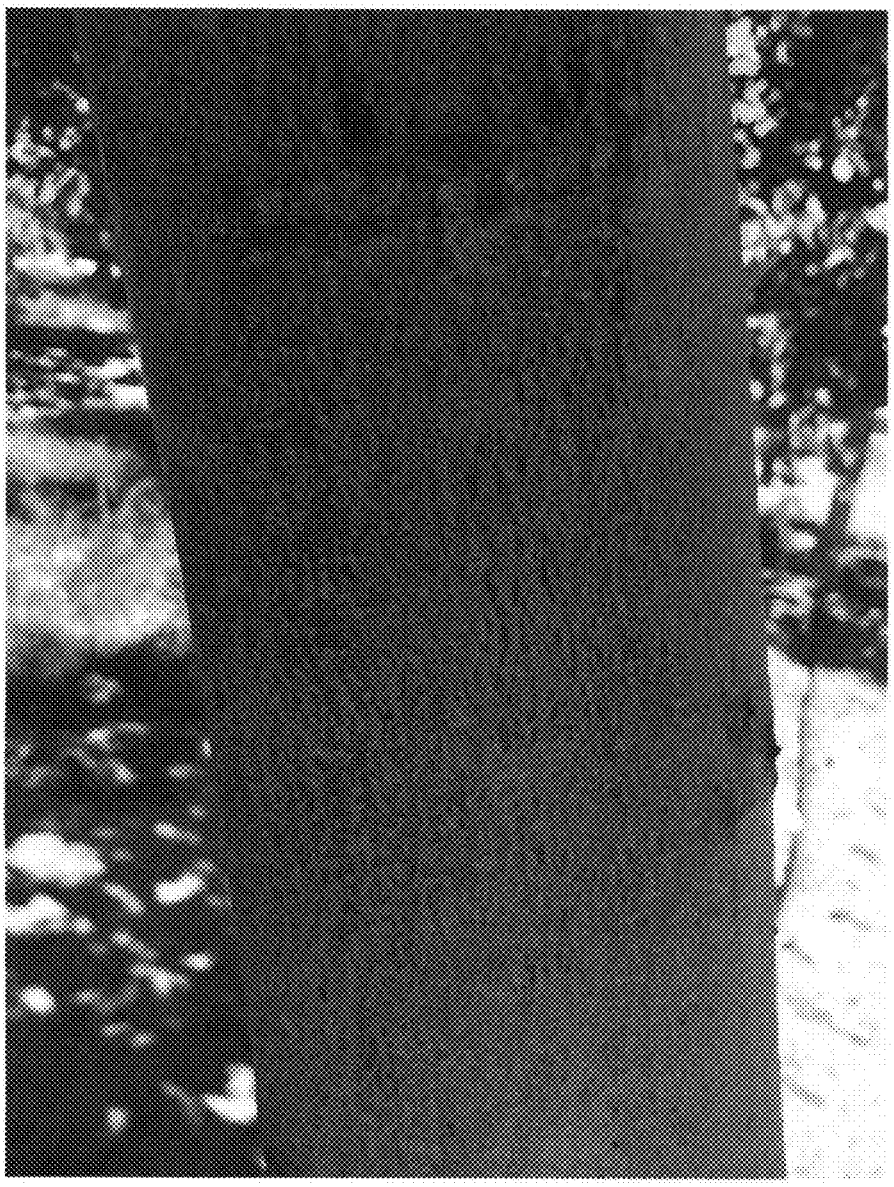
FIG. 3 illustrates the bark of a tree of walnut variety 'Durham'.

*Plant.*—The growth habit of 'Durham' is illustrated in FIG. 2. This 6 year old tree is approximately 5.5 m in height with a canopy diameter of 6.6 m. The trunk diameter at 0.5 m above the ground is approximately 12 cm. The silvery grey bark is typical of *Juglans regia*. The young bark is brown (2.5Y 5/2) and the older bark is grey (5Y 7.5/2) with raised lighter lenticels (2.5Y 8/2), illustrated in FIG. 3. Lenticels are round to oval in shape, and 1-5 mm×1-2 mm in size. 'Durham' has vigor similar to 'Chandler'.

Figure 4:
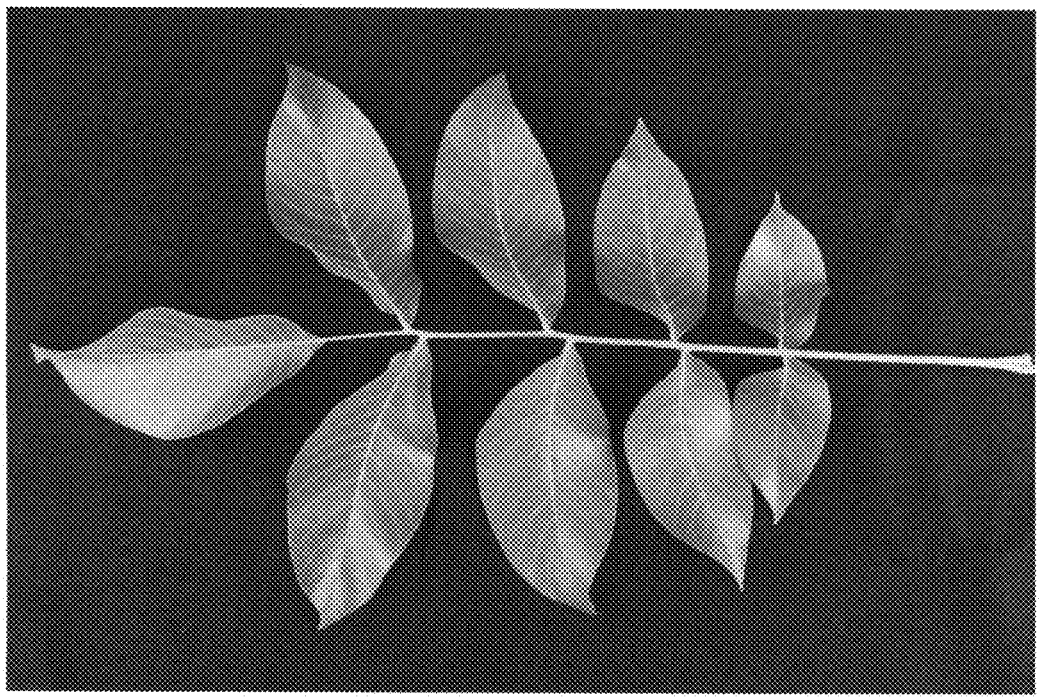
FIG. 4 illustrates an adaxial view of leaves of walnut variety 'Durham'.
Figure 5:
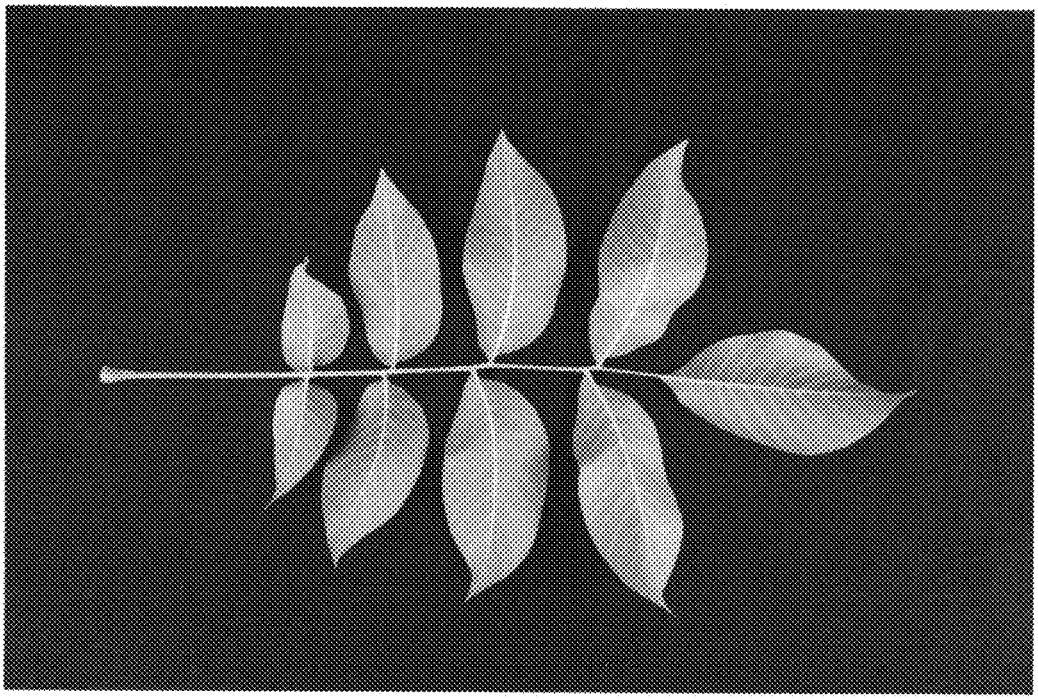
FIG. 5 illustrates an abaxial view of leaves of walnut variety 'Durham'.

*Foliage.*—The dark green foliage of 'Durham' is illustrated in FIG. 4 and FIG. 5, and is typical of *Juglans regia*. The average leafing out date between Years 7 and 23 has occurred on March 30$^{th}$ For comparative purposes, the leaf-out date of 'Chandler' is April 5$^{th}$. The typical leaf coloration of 'Durham' is green (adaxial 5GY 3/2, abaxial 5GY 5/2). The leaves are pinnately compound with 7-9 leaflets. The full leaf length is approximately 46 cm and the width is 30 cm. Leaflets are broadly elliptical and entire. The terminal leaflet averages 16 cm in length and 9 cm in width. The middle leaflets average 14 cm in length and 6 cm in width, and the proximal leaflets average 9 cm in length and 4 cm in width. The rachis averages 30 cm in length and 2-4 mm in diameter. Petiole length is 10 cm and is 2.5GY 6/6 in color.

Figure 6:
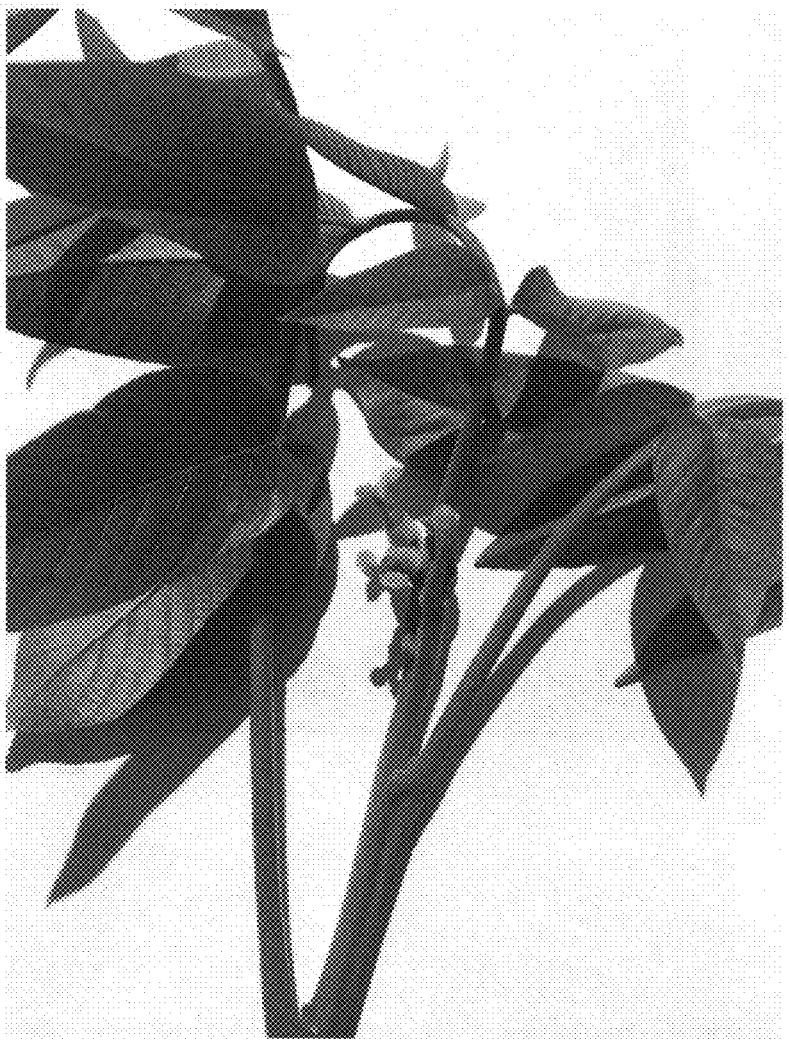
FIG. 6 illustrates female flowers of walnut variety 'Durham'.
Figure 7:
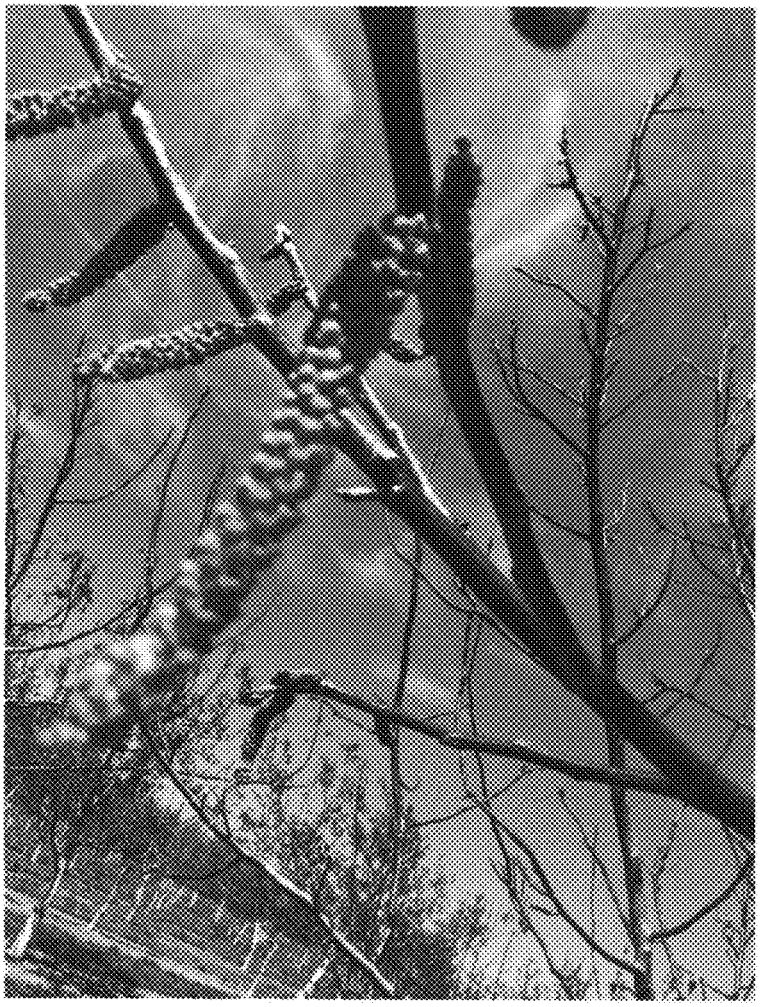
FIG. 7 illustrates catkins (male flowers) of walnut variety 'Durham'.

*Inflorescence.*—The 'Durham' tree is precocious, with first yield being noted at age 4 years. 'Durham' is not as precocious as 'Ivanhoe' and 'Solano', but 'Durham' trees yield abundantly at maturity. Male flowers (catkins) were first present at age 6 years. This delay in male maturity is typical of *Juglans regia*. From Years 6 to 23, average first female bloom occurred on April 13$^{th}$, peak bloom on April 18$^{th}$, and last bloom on April 23$^{rd}$. From Years 8 to 23, average male flowering (pollen shedding) began on March 29$^{th}$, peaked on April 4$^{th}$, and terminated on April 13$^{th}$. Pollen shedding in this protandrous variety does not cover pistillate bloom well, suggesting that a pollenizer would be needed for maximum yield. 'Chandler' would be a satisfactory pollenizer. The female flowers of 'Durham' are typical of *Juglans regia* (FIG. 6), with two flowers per inflorescence borne on 1 cm spikes at both terminal and lateral positions on current season's growth. Approximately 97% of the lateral buds contain inflorescences, making yields much greater than trees that only bear flowers terminally. A typical female flower of 'Durham' is approximately 8 to 10 mm at anthesis, and floral organs are typical of *Juglans regia*. The flowers appear vase-shaped when the 2 plumose stigmatic arms are curved outward. There are no petals. The female flowers are green (5GY 7/8) in color. The flower fragrance is typical of *Juglans regia*, and is not noticeably different than the foliage fragrance. The male flowers of 'Durham' (FIG. 7) are borne on catkins, are between 7 and 14 cm in length and 1-2 cm in diameter, and are green in color (5GY 7/10).

Figure 8:
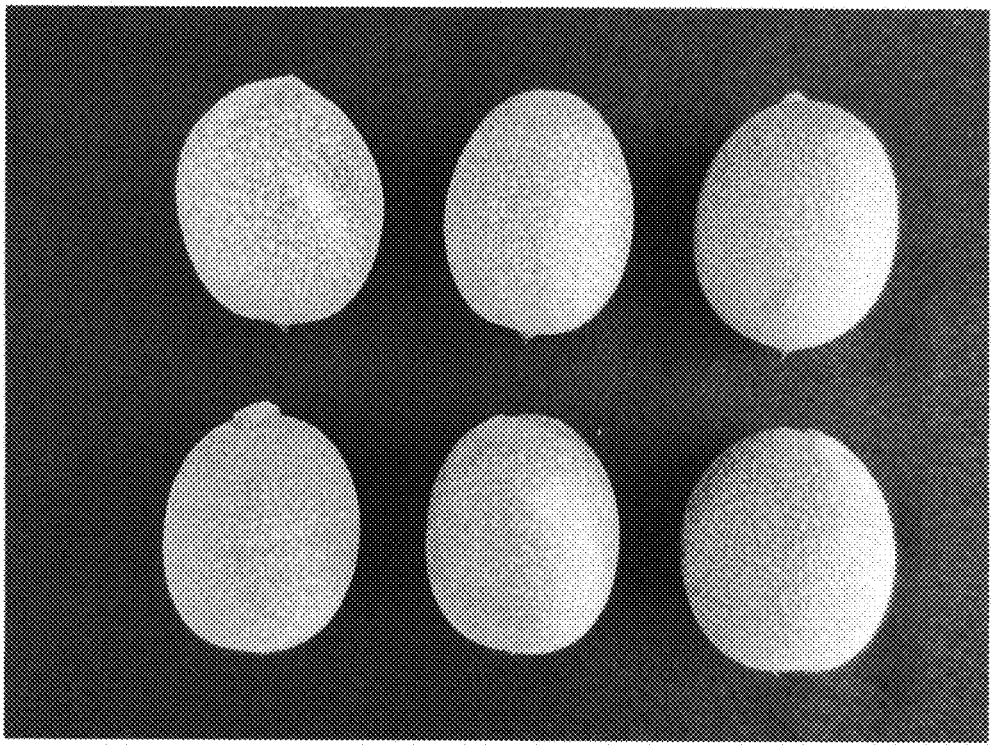
FIG. 8 illustrates hulls of walnut variety 'Durham' before opening and exposing the nuts.
Figure 9:
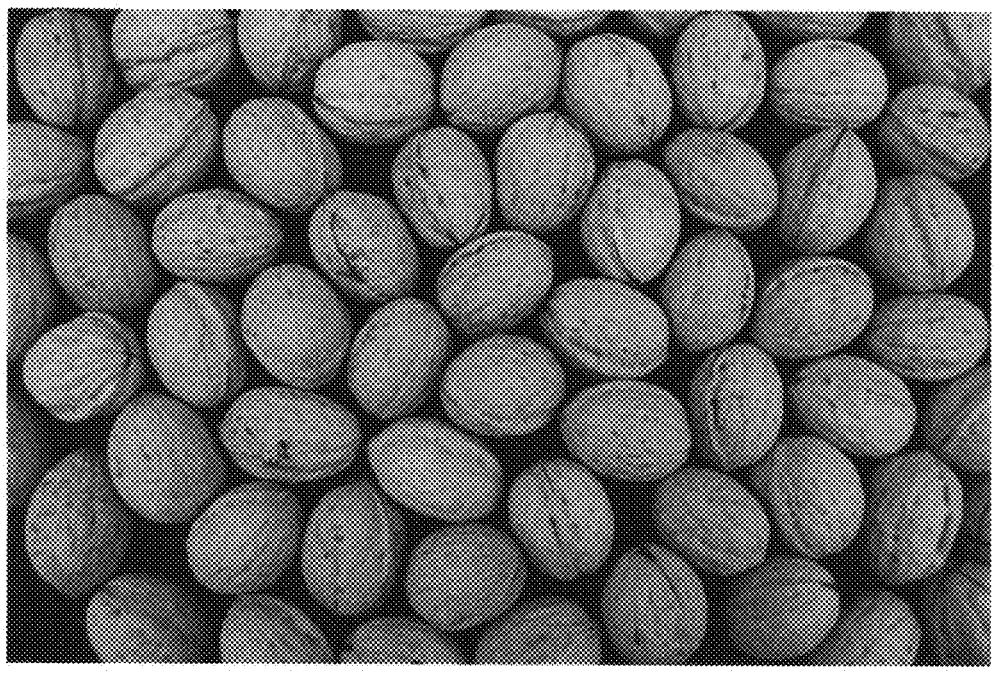
FIG. 9 illustrates nuts of walnut variety 'Durham'.
Figure 10A:
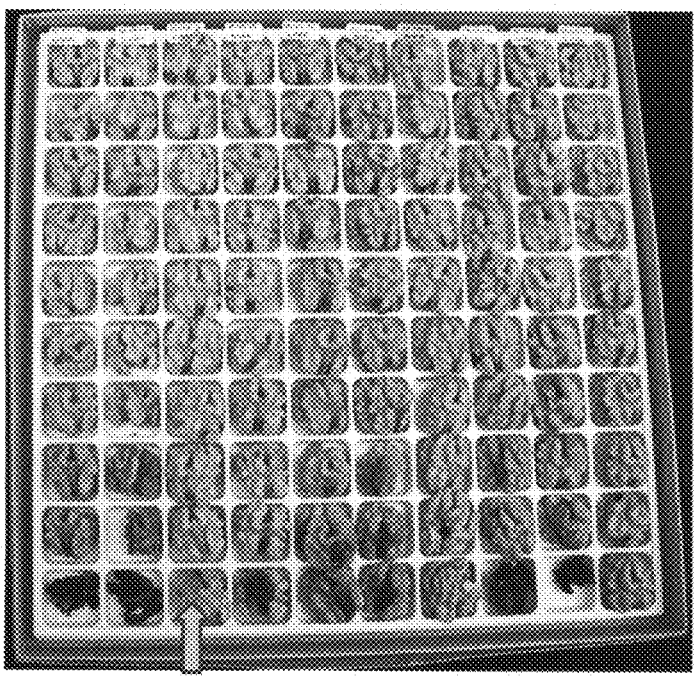
FIG. 10A and FIG. 10B illustrate kernels of walnut variety 'Durham'.
Figure 10B:
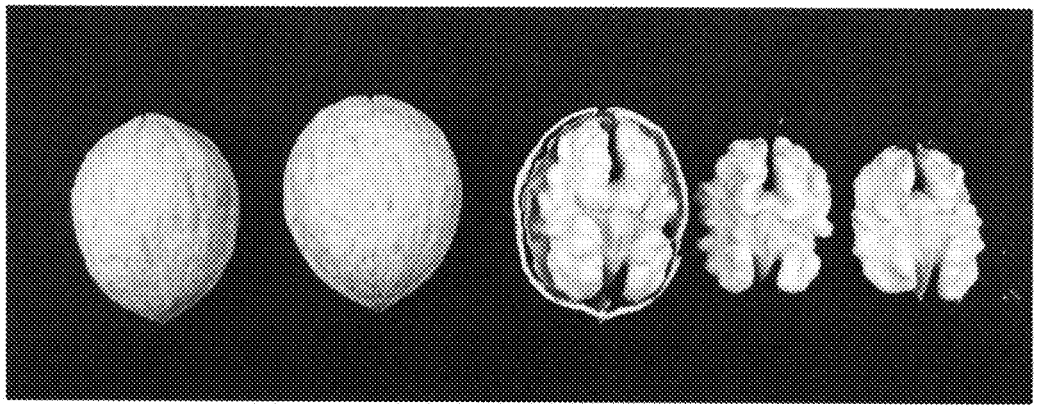

*Walnuts.*—'Durham' commonly harvests about 10 days before 'Chandler', about 10 days after 'Payne', and is similar in timing to 'Tulare' (U.S. Plant Pat. No. 8,268) and 'Howard', although 'Durham' has better kernel color and shell traits than these varieties. 'Durham' has excellent yields of mostly jumbo-sized walnuts. The hull is broadly elliptic, 6.0 cm×4.5 cm, 6 mm thick, and 2.5GY 6/6 in color, with numerous lighter speckles (FIG. 8). The nut is broadly elliptical, has a smooth, uniform and attractive appearance, is a lighter than average tan color (7.5YR 7/4) and measures approximately 48 mm in length and 35 mm in width (FIG. 9). The shell is 1.3 mm thick, relatively strong and well-sealed, suitable for in-shell marketing, and the kernel is easy to remove. The kernel weight averages 8.3 g and makes up 55% of the total nut weight of 15.1 g. Kernel fill of 'Durham' is better than 'Chandler' and 'Hartley'. Kernel color of 'Durham' is considered excellent (FIG. 10A and FIG. 10B), and scores mostly in the light to extra light categories of the USDA Standards for Grades of Shelled Walnuts, as determined by using the standard Walnut Color Chart for kernels published by the Dried Fruit Association of California (FIG. 11 and TABLE 2). In addition, kernels of 'Durham' have averaged 54.4 on the Relative Light Index used by Diamond Foods of Stockton, Calif. 'Durham' is typical of commercial walnuts in terms of flavor and firmness, the latter varying according to the percent moisture after drying.

*Disease susceptibility.*—'Durham' appears to be less susceptible to *Xanthomonas campestris* pv. *juglandis* than typical mid-season cultivars. Due to the relatively late leafing and flowering dates of 'Durham', closer to the cultivar 'Chandler' and later than recently released cultivars 'Ivanhoe' and 'Solano', 'Durham' will have less exposure to walnut blight caused by *Xanthomonas campestris* pv. *Juglandis*. Observed incidence of blight on 'Durham' has been low.

*Usage.*—'Durham' provides a mid-season harvesting walnut cultivar with high quality light-colored kernels, and nuts that can be used cracked or in-shell.

TABLE 1

Trial sites, locations, number of trees at location, and years of evaluation data collected for 'Durham'

| Trial Site | Location | Year Planted | # Durham Trees Evaluated | # Years of Data Collected | Comparison Cultivars Evaluated at Same Location |
|---|---|---|---|---|---|
| UC Davis-seedling block H | Davis | 3 | 1 | 8 | Chandler, Howard, Tulare, Hartley, Vina, Payne, PI159568 |
| Whitney Warren Ranch | Wheatland | 9 | 2 | 13 | Chandler, Howard, Tulare, Hartley, Vina, Ivanhoe, Solano |

TABLE 1-continued

Trial sites, locations, number of trees at location, and years of evaluation data collected for 'Durham'

| Trial Site | Location | Year Planted | # Durham Trees Evaluated | # Years of Data Collected | Comparison Cultivars Evaluated at Same Location |
|---|---|---|---|---|---|
| UCD Selection Block-B | Davis | 10 | 4 | 12 | Chandler, Howard, Tulare, Hartley, Vina, Payne, PI159568, Ivanhoe, Solano |
| CSU-Chico Selection Block | Chico | 10 | 4 | 12 | Chandler, Tulare, Hartley, Vina, Payne, Ivanhoe, Solano |
| KAC Selection Block | Parlier | 10 | 4 | 10 | Chandler, Howard, Tulare, Hartley, Vina, Payne |
| Sierra Gold Nurseries-SG | Yuba City | 12 | 10 | 3 | Solano, Ivanhoe |
| UCD Selection Block-D | Davis | 16 | 4 | 4 | Chandler, Howard, Tulare, Hartley, Vina, Payne, PI159568, Ivanhoe, Solano |
| Scheuring S505 C | Woodland | 18 | 4 | 5 | Chandler, Howard, Tulare, Ivanhoe, Solano |
| Stolp B | Durham | 19 | 33 | 3 | Chandler, Howard, Tulare, Ivanhoe, Solano |
| Scheuring S505 F | Woodland | 20 | 2 | 2 | Chandler, Howard, Tulare, Ivanhoe, Solano |

TABLE 2

Key to evaluation traits presented in FIG. 11

| | |
|---|---|
| Tree evaluation | |
| Catkin abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Nut and kernel traits | |
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | g |
| Kernel weight | g |

TABLE 2-continued

Key to evaluation traits presented in FIG. 11

| | |
|---|---|
| Kernel % | Kernel wt/inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA*) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like 'Chandler' |
| <50% shrivel | Percent of kernels with <50% shrivel |
| >50% shrivel | Percent of kernels with >50% shrivel |
| Veins % | Percent of kernels with conspicuous veins |

*"DFA" refers to the Dried Fruit Association of California.

What is claimed is:

1. A new and distinct variety of walnut tree designated 'Durham' as shown and described herein.

* * * * *

FIG. 11

For each trait - mean, number of observations combined for all locations and years, and standard error are shown

| | Durham | | | PI 159568 | | | Chandler | | | Howard | | | Tulare | | | Solano | | | Barley | | |
|---|---|---|---|---|---|---|---|---|---|---|---|---|---|---|---|---|---|---|---|---|---|
| | Mean | No. | SE | Mean | No. | SE | Mean | No. | SE | Mean | No. | SE | Mean | No. | SE | Mean | No. | SE | Mean | No. | SE |
| **Leafing date** | **3/30** | **35** | **1.36** | **3/20** | **20** | **0.87** | **4/5** | **75** | **0.84** | **4/4** | **39** | **1.28** | **4/3** | **40** | **0.13** | **3/25** | **38** | **1.24** | **4/4** | **32** | **1.07** |
| Days after Payne | 11 | 33 | 0.93 | 0 | 18 | 0.93 | 17 | 72 | 0.56 | 15 | 37 | 0.75 | 14 | 38 | 0.08 | 6 | 36 | 0.77 | 16 | 30 | 0.86 |
| Days after Chandler | -6 | 33 | 0.83 | -19 | 18 | 1.21 | 0 | 72 | 0.40 | -2 | 37 | 0.47 | -4 | 38 | 0.06 | -11 | 36 | 0.88 | -1 | 30 | 0.71 |
| 1st pollen | 3/29 | 27 | 1.49 | 3/26 | 17 | 1.21 | 4/6 | 72 | 0.90 | 4/5 | 33 | 1.49 | 4/6 | 36 | 0.14 | 3/29 | 27 | 1.28 | 4/5 | 27 | 1.35 |
| Peak pollen | 4/4 | 27 | 1.51 | 3/31 | 16 | 1.42 | 4/13 | 70 | 0.74 | 4/10 | 32 | 1.17 | 4/13 | 36 | 0.13 | 4/3 | 26 | 1.22 | 4/13 | 27 | 1.19 |
| Last pollen | 4/13 | 27 | 1.37 | 4/6 | 15 | 1.66 | 4/22 | 70 | 0.82 | 4/18 | 32 | 1.26 | 4/22 | 36 | 0.13 | 4/12 | 25 | 1.20 | 4/23 | 27 | 1.40 |
| 1st female bloom | 4/13 | 31 | 1.48 | 4/5 | 14 | 1.08 | 4/17 | 71 | 0.77 | 4/16 | 35 | 1.08 | 4/13 | 36 | 0.13 | 4/19 | 31 | 1.10 | 4/17 | 30 | 1.20 |
| Peak female bloom | 4/18 | 32 | 1.35 | 4/7 | 14 | 1.23 | 4/23 | 70 | 0.72 | 4/21 | 34 | 0.98 | 4/19 | 36 | 0.14 | 4/14 | 31 | 1.08 | 4/23 | 30 | 1.10 |
| Last female bloom | 4/23 | 31 | 1.29 | 4/10 | 14 | 1.34 | 4/30 | 69 | 0.76 | 4/27 | 34 | 0.97 | 4/25 | 36 | 0.12 | 4/19 | 30 | 1.19 | 4/29 | 30 | 1.15 |
| **Harvest date** | **9/24** | **57** | **0.74** | **9/13** | **12** | **2.07** | **10/8** | **186** | **0.59** | **9/29** | **64** | **0.76** | **9/27** | **59** | **0.12** | **9/22** | **76** | **0.89** | **10/4** | **49** | **0.88** |
| Days after Payne | 10 | 51 | 0.99 | -2 | 10 | 1.37 | 23 | 98 | 0.59 | 12 | 61 | 0.74 | 12 | 55 | 0.11 | 7 | 70 | 0.75 | 18 | 46 | 0.90 |
| Days after Chandler | -15 | 51 | 0.86 | -26 | 10 | 2.05 | -2 | 98 | 0.54 | -11 | 61 | 0.65 | -12 | 55 | 0.11 | -17 | 70 | 0.82 | -6 | 46 | 0.86 |
| Catkin abundance | 5.3 | 27 | 0.32 | 4.9 | 16 | 0.49 | 5.4 | 71 | 0.22 | 5.3 | 31 | 0.24 | 6.1 | 36 | 0.03 | 6.3 | 27 | 0.38 | 4.9 | 28 | 0.34 |
| Female abundance | 6.5 | 30 | 0.18 | 4.4 | 14 | 0.41 | 6.4 | 65 | 0.11 | 6.5 | 32 | 0.14 | 6.8 | 34 | 0.01 | 6.6 | 28 | 0.14 | 5.6 | 28 | 0.24 |
| **% lateral flowering** | **97.0** | **30** | **1.80** | **0.0** | **14** | **0.00** | **97.7** | **61** | **0.64** | **99.1** | **32** | **0.52** | **98.6** | **35** | **0.10** | **97.2** | **29** | **1.39** | **3.3** | **24** | **2.93** |
| **Yield** | **6.2** | **53** | **0.16** | **3.3** | **15** | **0.42** | **6.0** | **96** | **0.11** | **6.3** | **53** | **0.16** | **6.7** | **51** | **0.02** | **6.7** | **61** | **0.11** | **5.5** | **45** | **0.17** |
| Blight | 0.2 | 31 | 0.10 | 0.8 | 12 | 0.59 | 0.7 | 63 | 0.19 | 0.4 | 37 | 0.15 | 1.2 | 34 | 0.04 | 1.8 | 38 | 0.34 | 0.5 | 24 | 0.23 |
| Shell | | | | | | | | | | | | | | | | | | | | | |
| **Texture** | **4.2** | **63** | **0.08** | **5.0** | **3** | **0.58** | **4.9** | **101** | **0.03** | **5.6** | **65** | **0.07** | **5.2** | **61** | **0.01** | **4.9** | **71** | **0.04** | **5.3** | **50** | **0.07** |
| **Color** | **4.0** | **63** | **0.09** | **5.0** | **3** | **0.58** | **4.5** | **101** | **0.06** | **4.6** | **65** | **0.07** | **5.9** | **61** | **0.01** | **4.8** | **71** | **0.08** | **4.8** | **50** | **0.06** |
| Seal | 4.9 | 62 | 0.03 | 5.0 | 3 | 0.00 | 4.9 | 100 | 0.03 | 5.0 | 66 | 0.02 | 4.8 | 61 | 0.01 | 5.0 | 70 | 0.03 | 5.1 | 50 | 0.05 |
| Strength | 5.3 | 61 | 0.07 | 6.0 | 3 | 0.58 | 4.6 | 100 | 0.06 | 5.3 | 66 | 0.07 | 4.7 | 61 | 0.01 | 5.1 | 70 | 0.05 | 6.0 | 50 | 0.10 |
| Thickness | 1.3 | 62 | 0.01 | 1.3 | 3 | 0.03 | 1.3 | 100 | 0.01 | 1.4 | 66 | 0.01 | 1.2 | 61 | 0.01 | 1.3 | 70 | 0.01 | 1.5 | 50 | 0.02 |
| Kernel | | | | | | | | | | | | | | | | | | | | | |
| Inshell weight | 15.1 | 62 | 0.20 | 16.8 | 3 | 0.73 | 12.9 | 100 | 0.17 | 14.0 | 66 | 0.26 | 14.0 | 61 | 0.04 | 16.0 | 70 | 1.41 | 14.1 | 50 | 0.21 |
| **Kernel weight** | **8.3** | **62** | **0.13** | **8.8** | **3** | **0.18** | **6.4** | **100** | **0.09** | **7.1** | **66** | **0.14** | **7.5** | **61** | **0.02** | **7.9** | **70** | **0.12** | **6.4** | **50** | **0.12** |
| **Percent kernel** | **55.1** | **62** | **0.30** | **52.3** | **3** | **1.21** | **49.6** | **100** | **0.24** | **50.9** | **66** | **0.27** | **53.9** | **61** | **0.05** | **53.8** | **70** | **0.75** | **45.7** | **50** | **0.33** |
| Fill | 5.4 | 62 | 0.07 | 5.3 | 3 | 0.33 | 4.5 | 100 | 0.06 | 5.0 | 66 | 0.05 | 4.9 | 61 | 0.01 | 5.5 | 70 | 0.06 | 4.3 | 50 | 0.09 |
| Plumpness | 7.0 | 60 | 1.00 | 6.7 | 3 | 0.33 | 4.2 | 96 | 0.05 | 5.0 | 66 | 0.05 | 5.0 | 60 | 0.00 | 5.3 | 70 | 0.06 | 4.2 | 50 | 0.07 |
| Ease of Removal | 4.2 | 62 | 0.08 | 4.3 | 3 | 0.33 | 3.9 | 100 | 0.05 | 4.7 | 66 | 0.06 | 4.6 | 61 | 0.01 | 4.6 | 70 | 0.06 | 5.0 | 50 | 0.06 |
| % Extra light | 32.0 | 60 | 4.18 | 16.7 | 3 | 16.67 | 56.9 | 96 | 3.61 | 15.0 | 66 | 2.64 | 4.8 | 60 | 0.32 | 37.7 | 69 | 4.14 | 7.6 | 50 | 2.06 |
| % Light | 63.1 | 60 | 4.17 | 50.0 | 3 | 28.87 | 37.4 | 96 | 3.08 | 62.5 | 66 | 3.15 | 74.8 | 60 | 0.68 | 55.8 | 69 | 3.94 | 68.9 | 50 | 3.99 |
| % Tip shrivel | 12.6 | 60 | 2.01 | 14.4 | 3 | 9.88 | 29.8 | 96 | 2.44 | 3.5 | 66 | 1.17 | 6.0 | 60 | 0.24 | 8.9 | 69 | 1.85 | 0.0 | 50 | 0.00 |
| % Veins | 4.0 | 60 | 1.49 | 0.0 | 3 | 0.00 | 15.9 | 95 | 2.54 | 28.8 | 66 | 4.05 | 13.2 | 60 | 0.51 | 10.6 | 69 | 2.12 | 13.1 | 50 | 2.93 |